United States Patent
Hamacher et al.

(10) Patent No.: US 10,524,067 B2
(45) Date of Patent: Dec. 31, 2019

(54) HEARING ASSISTANCE SYSTEM

(71) Applicant: ADVANCED BIONICS AG, Staefa (CH)

(72) Inventors: Volkmar Hamacher, Hannover (DE); Stefan Fredelake, Hannover (DE); Phillipp Hehrmann, Hannover (DE)

(73) Assignee: Advanced Bionics AG, Staefa (CH)

( * ) Notice: Subject to any disclaimer, the term of this patent is extended or adjusted under 35 U.S.C. 154(b) by 277 days.

(21) Appl. No.: 15/545,299

(22) PCT Filed: May 11, 2015

(86) PCT No.: PCT/EP2015/060316
§ 371 (c)(1),
(2) Date: Jul. 20, 2017

(87) PCT Pub. No.: WO2016/180462
PCT Pub. Date: Nov. 17, 2016

(65) Prior Publication Data
US 2018/0014133 A1  Jan. 11, 2018

(51) Int. Cl.
*H04R 25/00* (2006.01)
*A61F 2/18* (2006.01)

(52) U.S. Cl.
CPC .......... *H04R 25/606* (2013.01); *A61F 2/18* (2013.01); *H04R 25/505* (2013.01);
(Continued)

(58) Field of Classification Search
CPC .... H04R 25/00; H04R 25/505; H04R 25/552; H04R 25/554; H04R 25/558; H04R 25/606
(Continued)

(56) References Cited

U.S. PATENT DOCUMENTS

| 5,479,522 A | 12/1995 | Lindemann et al. |
| 2008/0205659 A1 | 8/2008 | Fischer et al. |

(Continued)

FOREIGN PATENT DOCUMENTS

| WO | WO-2010/115227 | 10/2010 |
| WO | WO-2014/065831 | 5/2014 |
| WO | WO-2014/094859 | 6/2014 |

OTHER PUBLICATIONS

International Search Report and Written Opinion received in International Application No. PCT/US2015/060316, dated Jan. 15, 2016.
(Continued)

*Primary Examiner* — John P Lacyk
(74) *Attorney, Agent, or Firm* — ALG Intellectual Property, LLC

(57) ABSTRACT

There is provided a hearing assistance system, comprising an audio streaming device, a first hearing device for stimulating a first ear of a user, and a second hearing device for stimulating a second ear of the user, the audio streaming device comprising an audio input interface for receiving an input stereo audio signal, a unit for analyzing the input stereo audio signal in order to determine at least one azimuthal localization cue by comparing the two channels of the stereo signal, a unit for processing the input stereo audio signal in order to produce an output stereo audio signal, and a unit for supplying one channel of the output stereo audio signal to the first hearing device and for supplying the other channel of the output stereo audio signal to the second hearing device.

25 Claims, 4 Drawing Sheets

(52) U.S. Cl.
CPC ......... *H04R 25/552* (2013.01); *H04R 25/554* (2013.01); *H04R 25/558* (2013.01); *A61F 2002/183* (2013.01); *H04R 2225/67* (2013.01)

(58) Field of Classification Search
USPC .......................................................... 600/25
See application file for complete search history.

(56) References Cited

U.S. PATENT DOCUMENTS

| | | |
|---|---|---|
| 2009/0034744 A1 | 2/2009 | Van Loon et al. |
| 2012/0308019 A1 | 12/2012 | Edwards |
| 2014/0185850 A1 | 7/2014 | Fitz et al. |

OTHER PUBLICATIONS

Grantham, D. W. et al., "Interaural Time and Level Difference Thresholds for Acoustically Presented Signals in Post-Lingually Deafened Adults Fitted with Bilateral Cochlear Implants Using CIS+ Processing", *Ear and Hearing* 29, No. 1. (Jan. 2008), pp. 33-44.

Durlach, N. I. et al., "Interaural magnification", *J. Acoust. Soc. Am.* vol. 80, No. 6, pp. 1489 to 1850, 1986.

Kollmeier, B. et al., "Speech intelligibility enhancement by interaural magnification", *Acta Otolaryngol. Suppl.*, vol. 469, pp. 215 to 223, 1990.

HEARING ASSISTANCE SYSTEM

The invention relates to a hearing assistance system comprising an audio streaming device, a first hearing device for stimulating a first ear of a user and a second hearing device for stimulating a second ear of the user, wherein typically at least one of the hearing devices is a cochlear implant (CI) device. The hearing assistance system is suitable for presenting a stereo audio signal to the user.

Usually, it is a desirable feature of hearing assistance systems to enable satisfactory stereophonic perception of music. However, for example, for CI users stereophonic perception of music via two separated loudspeakers is limited, since in the usual CI coding strategies the interaural time differences ("ITD") (or, in the frequency domain, the corresponding interaural phase differences ("IPD")) are not coded in the electrical stimulation signal due to the envelope-based processing. Furthermore, the ability of CI users to finely discriminate interaural level differences ("ILDs") is reduced compared to normal hearing listeners, most likely owing to the substantially reduced dynamic range of possible stimulation levels in electric hearing. An example of a study concerning ITD and ILD perception by CI users is found in "Interaural Time and Level Difference Thresholds for Acoustically Presented Signals in Post-Lingually Deafened Adults Fitted with Bilateral Cochlear Implants Using CIS+ Processing.", by D. W. Grantham et al., Ear and Hearing 29, no. 1 (January 2008), pages 33-44.

In general, localization of sound sources by the human hearing is primarily based on two spatial cues, namely the ITDs in a low frequency range (below approximately 1500 Hz) and ILDs in an upper frequency range. Rather than presenting a stereo signal to a hearing device user via room loudspeakers, such stereo signal may be presented to the user by streaming a corresponding stereo audio signal to the hearing devices via a streaming device, with the left channel of the signal being transmitted to the left ear hearing device and with the right channel being transmitted to the right ear hearing device. In other words, a streaming device may be used for relaying a stereo audio signal to the hearing devices via a wireless audio link.

It is generally known that binaural cues, namely ILDs and ITDs, may be enhanced by appropriate audio signal processing, see for example the Article "Interaural magnification" by N. I. Durlach et al., J. Acoust. Soc. Am. Vol. 80, No. 6, pages 1489 to 1850, 1986, and the Article "Speech intelligibility enhancement by interaural magnification" by B. Kollmeier et al., Acta Otolaryngol. Suppl., Vol. 469, pages 215 to 223, 1990.

WO 2010/115227 A1 relates to a binaural hearing assistance system comprising, for example, two CI devices, wherein the audio signal captured by each of the hearing devices via its local microphone are binaurally processed in a manner so as to enhance localization cues; in particular, an ITD may be represented as an ILD in the processed signal, and a localization cue detected in a certain frequency band may be inserted into the processed signal in a different frequency band. Thereby, the localization of a sound source by the user of the hearing devices may be improved.

US 2009/0034744 A1 relates to a method for "widening" of a stereo signal, for example in home cinemas or sound systems in a car, where the loudspeaker placement often is not optimal due to, for example, restricted space. To this end, the stereo signal is processed in a manner so as to transform the ILDs to the desired value; for example, if the loudspeakers are located too close together, the ILDs may be enhanced in order to improve stereo perception.

It is an object of the invention to optimize stereo perception by the user of a hearing assistance system, while power consumption in the hearing devices is kept relatively low. It is a further object to provide for corresponding hearing assistance method.

According to the invention, these objects are achieved by hearing assistance system as defined in claim 1 and a method as defined in claim 25, respectively.

The invention is beneficial in that, by enhancing binaural cues by appropriate audio signal processing in an audio streaming device, stereo perception of the hearing device user, in particular in case that at least one of the hearing devices is a CI device, can be enhanced, while no additional power consumption is required in the hearing devices; rather, the additional signal processing required for the enhancement of binaural cues is performed in the streaming device, which can be provided with a much larger battery than the hearing devices.

Preferred embodiments of the invention are defined in the dependent claims.

Hereinafter, examples of the invention will be illustrated by reference to the attached drawings, wherein.

Figure 1:
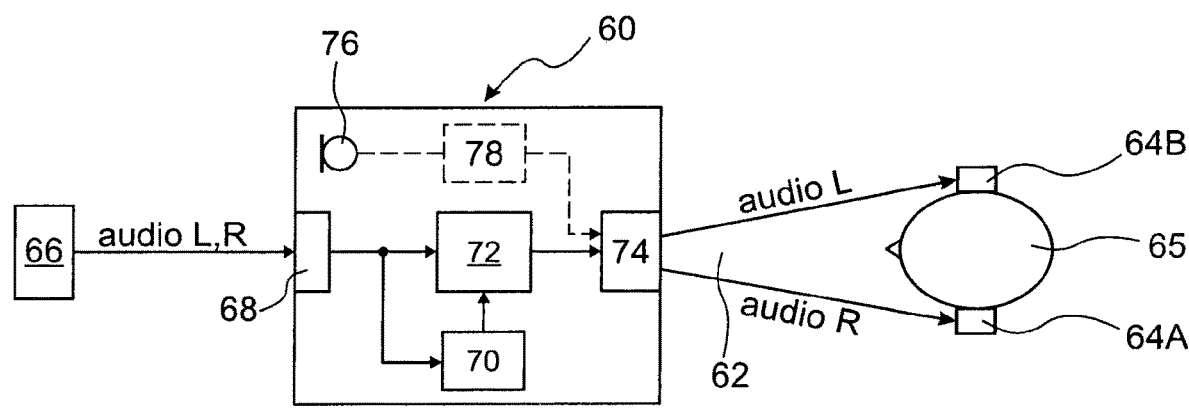
FIG. 1 is a schematic representation of an example of a hearing assistance system according to the invention.

FIG. 1 is a schematic representation of a hearing assistance system according to the invention, comprising a right ear hearing device 64A worn at the right ear of a user 65, a left ear hearing device 64B worn at the left ear of the user 65 and an audio streaming device 60, which receives an input stereo audio signal from an audio source 66 via an audio input interface 68. The audio streaming device 60 further comprises a unit 70 for analyzing the input stereo audio signal in order to determine at least one azimuthal angular localization cue by comparing the two channels of the input stereo audio signal, a unit 72 for processing the input stereo audio signal in order to produce an output stereo audio signal, and a unit 74 for supplying one channel of the output stereo audio signal to the right ear hearing device 64A and for supplying the other channel of the output stereo audio signal to the left ear hearing device 64A. The processing unit 72 is adapted to process the input stereo audio signal, based on the determined at least one azimuthal localization cue, in a manner so as to enhance a stereo effect perceived by the user 65 of the hearing devices 64A, 64B when stimulated by the output stereo signal, compared to stimulation by the input stereo signal. In other words, the processing unit 72 provides for a stereo enhancement.

The streaming device 60 may be, for example, a body worn device (such as worn by a loop around the user's neck or to be fixed at the user's clothes) or a handheld device. In particular, the streaming device 60 may comprise at least one microphone 76 for acting as a wireless microphone for the hearing devices 64A, 64B in order to capture, for example, another person's voice speaking to the user 65 of the hearing devices 64A, 64B. The audio signal captured by the microphone 76, is supplied, after appropriate processing in an audio signal processing unit 78, to the unit 74 for being transmitted to the hearing devices 64A, 64B. The unit 74 typically is a wireless audio output interface for transmitting the signals via a wireless link 62 to the hearing devices 64A, 64B; typically the output interface 74 is an inductive interface or a 2.4 GHz interface which may use e.g. a Bluetooth protocol or a proprietary protocol.

The input interface 68 likewise may be a wireless interface, such as a Bluetooth interface, or it may be a plug-in interface for a wired connection.

Preferably, at least one of the hearing devices MA, 64B is an auditory prosthesis, in particular a CI device. According to one embodiment, both hearing devices 64A, 64B may be CI devices; according to an alternative embodiment, one of the hearing devices may be a CI device and the other one may be a hearing aid or a bone conduction implant in order to realize a bimodal system. While the embodiments comprising at least one CI device are preferred, the invention in principle also is applicable to embodiments wherein both hearing devices are hearing aids. Further, one of the hearing devices or both hearing devices may be a bimodal device, preferably an EAS (electro-acoustic stimulation) device providing for both electrical and acoustic stimulation of the same ear.

Figure 2:
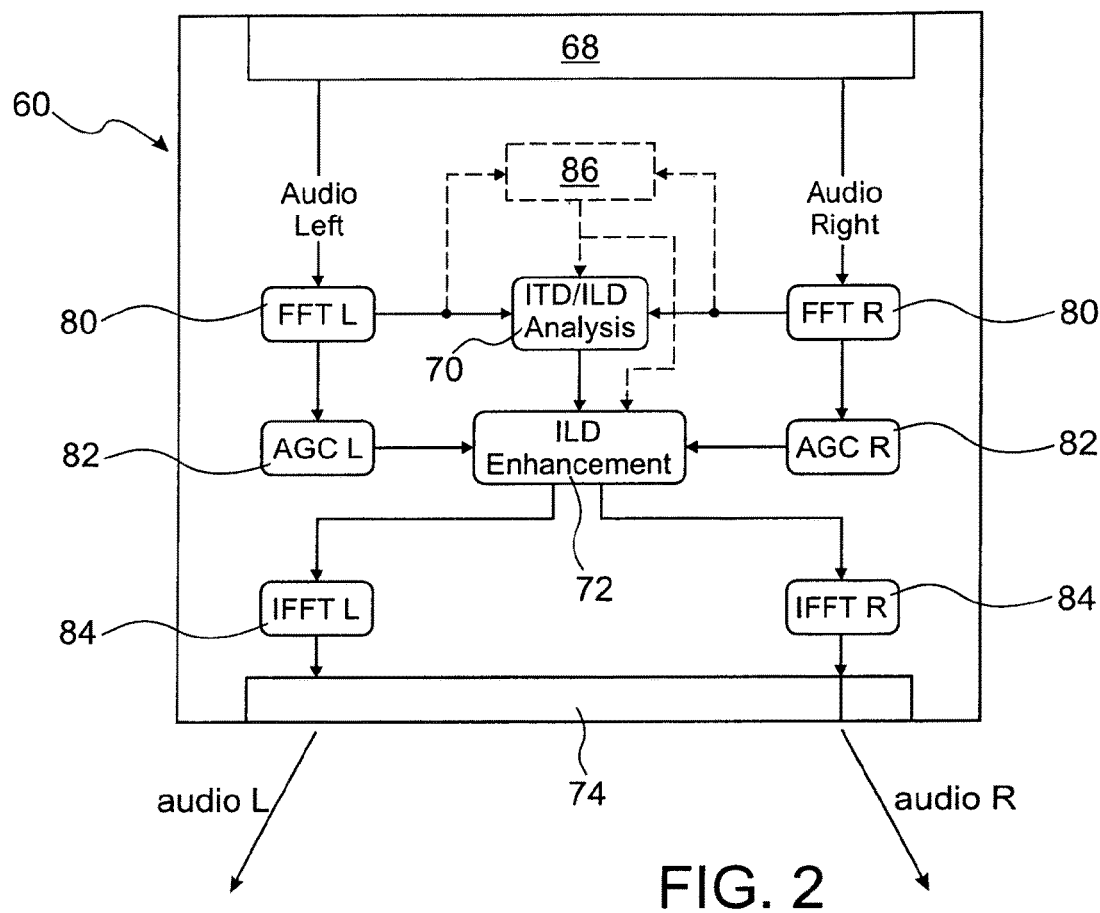
FIG. 2 is a schematic representation of an example of the audio signal processing in an audio streaming device to be used with the invention.

An example of the processing of the input stereo signal in the audio streaming device 60 is shown in FIG. 2, according to which each stereo channel received via the input interface 68 first is transformed into the frequency domain by a FFT unit 80. The frequency domain signal then is supplied both to an AGC ("automatic gain control") unit 82 and to the analysis unit 70. The signal leaving the respective AGC unit 82 is supplied to the processing unit 72 for stereo enhancement according to the binaural cues extracted by the analysis unit 70. The signal leaving the processing unit 72 is supplied to a re-transformation unit 84 where it undergoes an inverse FFT for being retransformed into the time domain. The time domain signal then is supplied to the output interface 74 for being supplied to the hearing devices 64A, 64B.

Preferably, the streaming device 60 comprises a classifier unit 86 which analyzes the stereo input signal in the frequency domain in order to determine whether the input stereo audio signal is a music signal or not. The stereo enhancement processing in the processing unit 72 is enabled by the classifier unit 86 only during times when the input stereo signal is determined to be a music signal.

In the example of FIG. 2, the at least one azimuthal localization cue comprises the interaural phase differences IPDs (which are closely related to the ITDs in the time domain) in a lower frequency range, i.e. typically at frequencies below a first threshold frequency, which may be from 500 Hz to 2000 Hz, typically around 1500 Hz. The processing unit 72 then transforms these extracted IPDs into interaural level differences ILDs in order to process the input stereo audio signal by applying these ILDs in a lower frequency range, i.e. at frequencies below a second threshold frequency, which typically is from 500 Hz to 2000 Hz and which preferably equals the first threshold frequency.

Such coding of the IPDs into ILDs in the low frequency range is particularly relevant for CI users, since the IPDs usually are not perceivable by CI users, whereas CI users may perceive the corresponding "artificial" ILDs in the lower frequency range.

Further, the analysis unit 70 determines the ILDs as a further azimuthal localization cue, wherein the processing unit 72 is adapted to process the input stereo audio signal by increasing the ILDs of the input stereo audio signal. The magnitude of this increase may be chosen such that it compensates for the expected reduction of the ILDs effected by the AGC unit 82. It may further be chosen to "overcompensate" the expected reduction, i.e. to amplify the ILDs in the output signal even beyond the naturally-occurring range, Thereby, the potential reduction of the azimuthal localization ability by the CI user due to reduced ILDs caused by AGC processing and an overall reduced sensitivity to ILDs may be prevented. Typically, such AGC compensation processing is applied to a higher frequency range, i.e. at frequencies above a third threshold frequency, which typically may be from 500-2000 Hz in embodiments in which, like in the case of FIG. 2, the AGC units are provided as part of the streaming device 60, the hearing devices 64A, 64B preferably are adapted to operate in a music mode when receiving the stereo audio signal from the streaming device 60, in which music mode a dedicated linear gain setting may be applied in order to avoid potential artifacts arising from imperfect coordination between the streaming device and the audio signal processing in the hearing devices 64A, 64B.

According to an alternative embodiment, the AGC units may be provided as part of the hearing devices 64A, 64B, as will be hereinafter illustrated by reference to FIG. 4, with a corresponding example of the stereo signal processing in the streaming device 60 suitable for such case being shown in FIG. 5, wherein the AGC units 82 of FIG. 2 are omitted. However, in FIG. 5 an additional block 88 is shown which provides information concerning the AGC setting in the hearing devices 64A, 64B to the processing unit 72 for enabling the processing unit 72 to compensate for the ILD reduction caused by the AGC processing.

In case that both hearing devices 64A, 64B are hearing aids, it may be beneficial to enhance not only the ILDs but also the IPDs, since hearing aid users typically are able to perceive IPDs.

Figure 3:
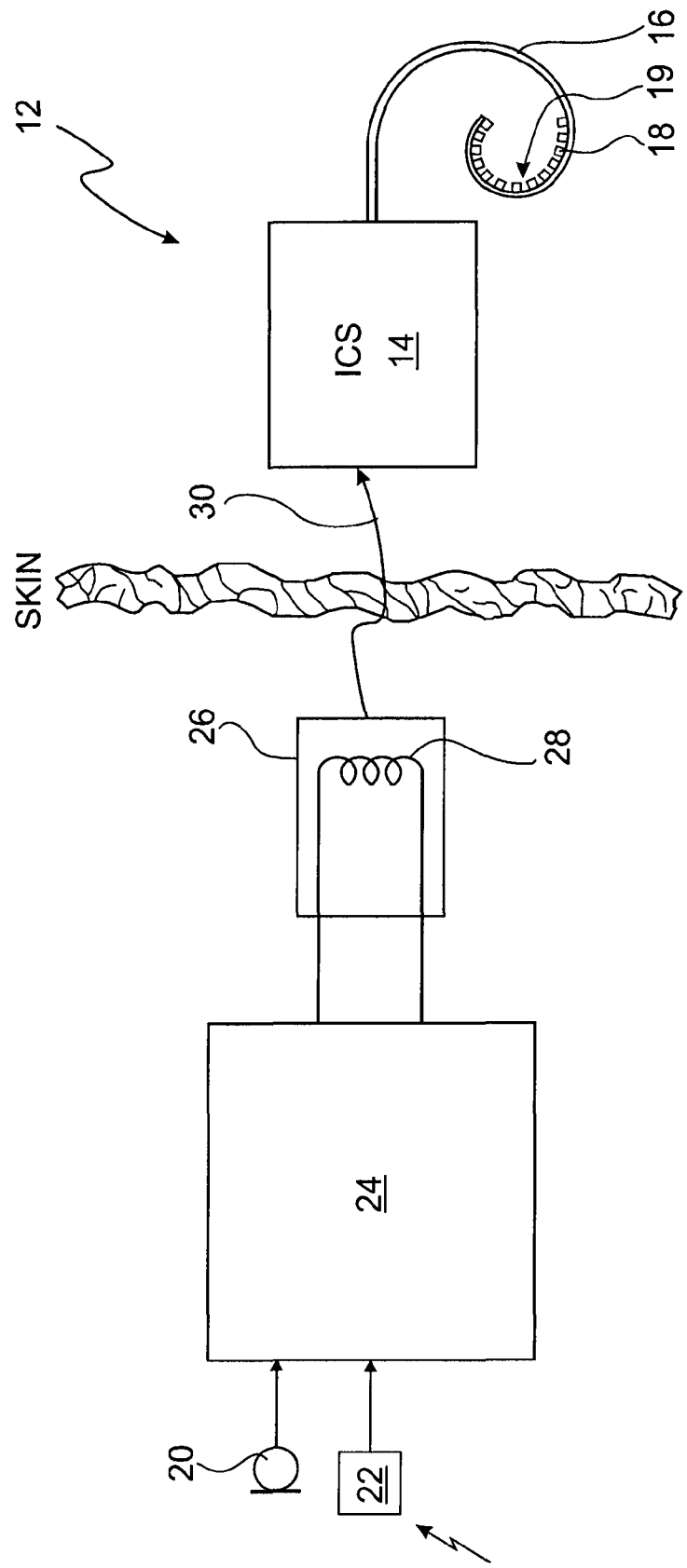
FIG. 3 is a schematic representation of an example of a CI device to be used with the invention.
Figure 4:
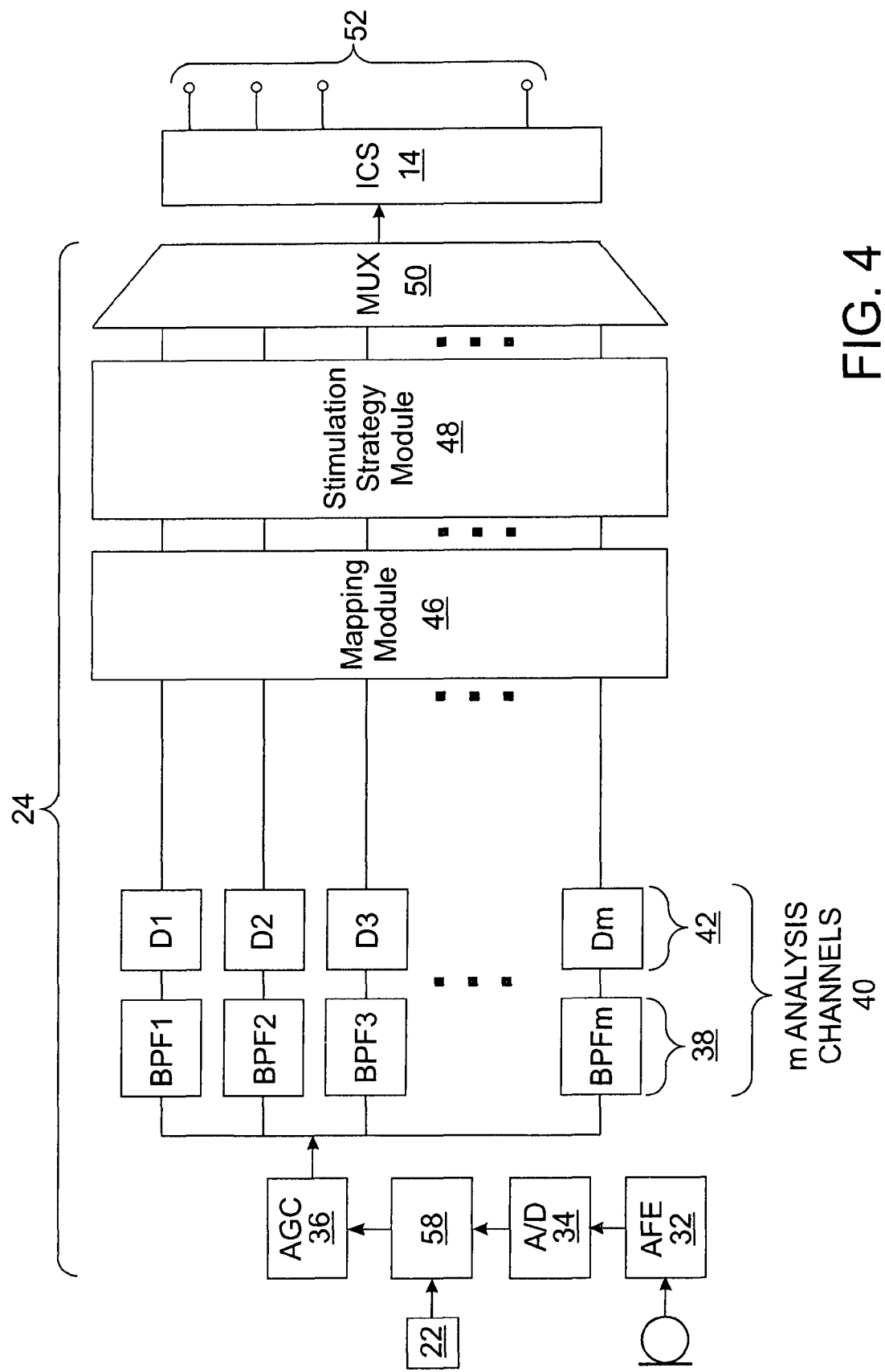
FIG. 4 is a block diagram of an example of the signal processing structure of the CI device of FIG. 3.
Figure 5:
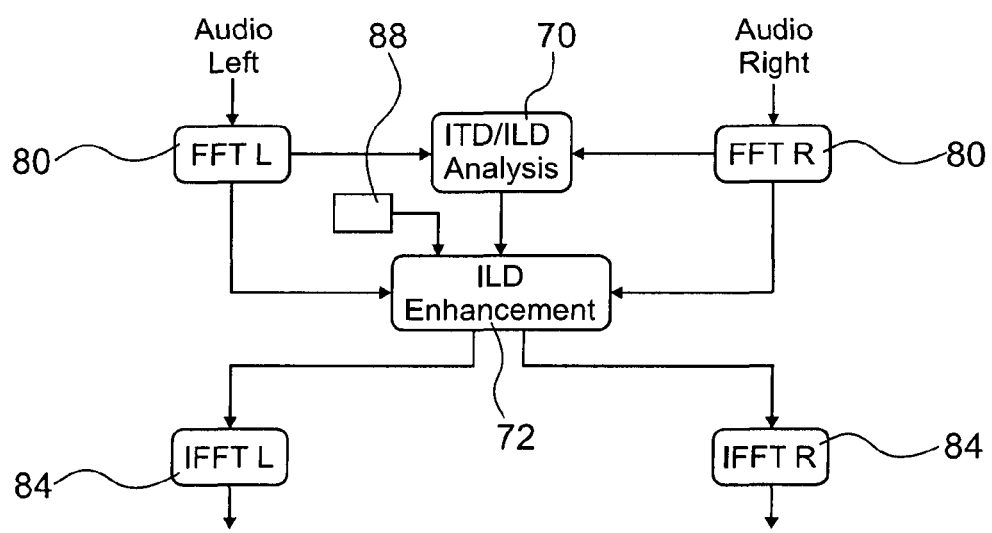
FIG. 5 is a representation like FIG. 2, wherein, however, an alternative embodiment is shown.

In FIGS. 3 and 4 an example of a CI device to be used with the invention is shown schematically. The system comprises a sound processing sub-system 10 and a stimulation sub-system 12. The sound processing sub-system 10 serves to detect or sense an audio signal and divide the audio signal into a plurality of analysis channels each containing a frequency domain signal (or simply "signal") representative of a distinct frequency portion of the captured audio. A signal level value is determined for each analysis channel by analyzing the respective frequency domain signal. Stimulation parameters are generated based on the frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlea of a patient in accordance with the stimulation parameters received from the sound processing sub-system 10. Electrical stimulation is provided to the patient via a CI stimulation assembly 18 comprising a plurality of stimulation channels.

In the example shown in FIG. 3, the stimulation sub-system 12 comprises an ICS 14, a lead 16 and the stimulation assembly 18 disposed on the lead 16. The stimulation assembly 18 comprises a plurality of "stimulation contacts" 19 for electrical stimulation of the auditory nerve. The stimulation assembly 18 may be inserted within a duct of the cochlea in such a manner that the stimulation contacts 19 are in communication with one or more stimulation sites within the cochlea, i.e. the stimulation contacts 19 are adjacent to, in the general vicinity of, in close proximity to, directly next to, or directly on the respective stimulation site.

In the example shown in FIG. 3, the sound processing sub-system 10 comprises at least one microphone 20 for capturing audio signals from ambient sound, a wireless interface 22 for receiving an audio stream from a streaming device 60 via a wireless link 62, a sound processor unit 24 which receives audio signals from the microphone 20 and the wireless interface 22 and a headpiece 26 having a coil 28 disposed therein. The sound processor unit 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 3 the sound processor unit 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links.

The sound processor unit 24, the microphone 20 and the wireless interface 22 together form part of a sound processor module 25 to be worn behind the ear, as will be explained hereinafter in more detail by reference to FIGS. 3 and 4.

In FIG. 4 a schematic example of a sound processor unit 24 is shown. The audio signals captured by the microphone 20 are amplified in an audio front end circuitry 32, with the amplified audio signal being converted to a digital signal by an analog-to-digital converter 34. Both the signal from the microphone 20 and the demodulated audio signal received via the wireless interface 22 are supplied as input signals to a unit 58 which generates a single output signal from these two input signals, which output signal is supplied to an automatic gain control (AGC) unit 36.

After appropriate automatic gain control, the digital signal is subjected to a filterbank 38 comprising a plurality of filters F1 . . . Fm (for example, band-pass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then arranging the resulting frequency bins into the analysis channels 40.

The signals within each analysis channel 40 are input into an envelope detector 42 in order to determine the amount of energy contained within each of the signals within the analysis channels 40 The output signals of the envelope detectors 42 are supplied to a mapping module 46 which serves to map the signals in the analysis channels 40 to the stimulation channels S1 . . . Sn. For example, signal levels may be mapped to amplitude values used to define the electrical stimulation pulses that are applied to the patient by the ICS 14 via M stimulation channels 52. For example, each of the m stimulation channels 52 may be associated to one of the stimulation contacts 19 (FIG. 3) or to a group of the stimulation contacts 19.

The sound processor unit 24 further comprises a stimulation strategy module 48 which serves to generate one or more stimulation parameters based on the signals in the analysis channels 40 and in accordance with a certain stimulation strategy (which may be selected from a plurality of stimulation strategies). For example, stimulation strategy module 48 may generate stimulation parameters which direct the ICS 14 to generate and concurrently apply weighted stimulation currents via a plurality 52 of the stimulation channels S1 . . . Sn in order to effectuate a current steering stimulation strategy. Additionally, or alternatively, the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor unit 24 also comprises a multiplexer 50 which serves to serialize the stimulation parameters generated by the stimulation strategy module 48 so that they can be transmitted to the ICS 14 via the communication link 30, i.e. via the coil 28.

The invention claimed is:

1. A hearing assistance system, comprising:
an audio streaming device, a first hearing device for stimulating a first ear of a user, and a second hearing device for stimulating a second ear of the user,
the audio streaming device comprising
an audio input interface for receiving, directly from an audio source other than the first and second hearing devices, an input stereo audio signal comprising a first channel and a second channel,
a unit for analyzing the input stereo audio signal in order to determine at least one azimuthal localization cue by comparing the first and second channels of the input stereo audio signal,
a unit for processing the input stereo audio signal in order to produce an output stereo audio signal, and
a unit for supplying one channel of the output stereo audio signal to the first hearing device and for supplying the other channel of the output stereo audio signal to the second hearing device,
wherein the processing unit is adapted to process the input stereo audio signal, based on the determined at least one azimuthal localization cue, in a manner so as to enhance a stereo effect perceived by the user of the hearing devices when stimulated by the output stereo audio signal, compared to stimulation by the input stereo audio signal.

2. The system of claim 1, wherein at least one of the first hearing device and the second hearing device is an auditory prosthesis.

3. The system of claim 2, wherein the first hearing device and the second hearing device are cochlear implant devices.

4. The system of claim 2, wherein the first hearing device is a cochlear implant device and the second hearing device is a hearing aid, a bone conduction stimulation device or a middle-ear implant.

5. The system of claim 2, wherein at least one of the first hearing device and the second hearing device is a bimodal stimulation device.

6. The system of claim 2, wherein the at least one azimuthal localization cue comprises at least one of the interaural time differences and the interaural phase differences at frequencies below a first threshold frequency, and wherein the processing unit is adapted to transform said interaural time differences and/or interaural phase differences into interaural level differences to process the input stereo audio signal by applying said interaural level differences at frequencies below a second threshold frequency.

7. The system of claim 6, wherein the first threshold frequency is from 500 Hz to 2000 Hz.

8. The system of claim 6, wherein the second threshold frequency is from 500 Hz to 2000 Hz.

9. The system of claim 6, wherein the first threshold frequency equals the second threshold frequency.

10. The system of claim 1, wherein the system further comprises an AGC unit for each of the first and second channels in order to apply automatic gain control to each of the first and second channels, wherein the at least one azimuthal localization cue comprises interaural level differences, and wherein the processing unit is adapted to process the input stereo audio signal by increasing the interaural level differences of the input stereo audio signal in a manner so as to at least compensate for an expected reduction of the interaural level differences due to action of the AGC units on the first and second channels.

11. The system of claim 10, wherein the processing unit is adapted to increase the ILDs of the input stereo audio signal above a third threshold frequency.

12. The system of claim 11, wherein the third threshold frequency is from 500 to 2000 Hz.

13. The system of claim 10, wherein the AGC units form part of the streaming device.

14. The system of claim 13, wherein the hearing devices are adapted to operate in a music mode when receiving the output stereo audio signal from the streaming device.

15. The system of claim 14, wherein the music mode includes a linear gain setting.

16. The system of claim 10, wherein each hearing device comprises one of the AGC units.

17. The system of claim 1, wherein the streaming device comprises a classifier unit for detecting, by analyzing the input stereo audio signal, whether the input stereo audio signal is a music signal, and wherein the processing unit is adapted to process the input stereo audio signal in said manner so as to enhance a stereo effect perceived by the user of the hearing devices only in case that a music signal is detected.

18. The system of claim 1, wherein streaming device is adapted to transform the input stereo audio signal into the frequency domain prior to being supplied to analyzing unit and the processing unit.

19. The system of claim 1, wherein the streaming device is designed as a body-worn device or a handheld device.

20. The system of claim 1, wherein the streaming device comprises a wireless audio output interface for transmitting the output stereo audio signal via a wireless link to the hearing devices.

21. The system of claim 20, wherein the wireless audio output interface is an inductive interface or a 2.4 GHz interface.

22. The system of claim 20, wherein the streaming device comprises at least one microphone for acting as a wireless microphone for the hearing devices, and wherein the streaming device is adapted to transmit audio signals captured by the at least one microphone via the wireless audio output interface to the hearing devices.

23. The system of claim 1, wherein the audio input interface is a wireless interface.

24. The system of claim 23, wherein the audio input interface is a Bluetooth interface.

25. A method of providing a stereo audio signal to a user wearing a first hearing device at a first ear and a second hearing device at a second ear, comprising:
  receiving, by an audio input interface of an audio streaming device directly from an audio source other than the first and second hearing devices, an input stereo audio signal comprising a first channel and a second channel,
  analyzing, by an analyzing unit of the streaming device, the input stereo audio signal in order to determine at least one azimuthal localization cue by comparing the two channels of the input stereo audio signal,
  processing, by a processing unit of the streaming device, the input stereo audio signal, based on the determined at least one azimuthal localization cue, in order to produce an output stereo audio signal in a manner so as to enhance a stereo effect perceived by the user of the hearing devices when stimulated by the output stereo audio signal, compared to stimulation by the input stereo audio signal, and
  supplying one channel of the output stereo audio signal to the first hearing device and supplying the other channel of the output stereo audio signal to the second hearing device.

* * * * *